United States Patent [19]

Dessau et al.

[11] Patent Number: 5,124,497
[45] Date of Patent: Jun. 23, 1992

[54] PRODUCTION OF MONO-SUBSTITUTED ALKYLAROMATICS FROM $C_8+$ N-PARAFFINS

[75] Inventors: Ralph M. Dessau, Edison, N.J.; Ernest W. Valyocsik, Yardley, Pa.; Randall D. Partridge, W. Trenton, N.J.

[73] Assignee: Mobil Oil Corporation, Fairfax, Va.

[21] Appl. No.: 419,928

[22] Filed: Oct. 11, 1989

[51] Int. Cl.[5] .................................... C07C 2/52
[52] U.S. Cl. ............................................. 585/419
[58] Field of Search ..................................... 585/419

[56] References Cited

U.S. PATENT DOCUMENTS

| Re. 29,948 | 3/1979 | Dwyer et al. | 208/110 |
|---|---|---|---|
| 3,631,215 | 12/1971 | Clippinger et al. | 585/419 |
| 3,702,293 | 11/1972 | Hayes et al. | 208/139 |
| 3,702,294 | 11/1972 | Rausch | 208/139 |
| 3,821,105 | 6/1974 | Mitsche et al. | 585/419 |
| 3,878,131 | 4/1975 | Hayes | 252/466 PT |
| 3,892,657 | 7/1975 | Wilhelm | 585/419 |
| 3,960,710 | 6/1976 | Pollitzer et al. | 502/227 |
| 4,104,320 | 8/1978 | Bernard et al. | 585/419 |
| 4,110,200 | 8/1978 | Antos | 585/419 |
| 4,115,253 | 9/1978 | Adams et al. | 585/419 |
| 4,214,980 | 7/1980 | LePage et al. | 585/419 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,417,083 | 11/1983 | Bernard et al. | 585/419 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,849,567 | 7/1989 | Dessau et al. | 585/379 |
| 4,867,864 | 9/1989 | Dessau et al. | 585/413 |
| 4,868,145 | 9/1989 | Dessau et al. | 502/71 |

FOREIGN PATENT DOCUMENTS

| 74651 | 7/1982 | European Pat. Off. | |
| 0107389 | 4/1984 | European Pat. Off. | |
| 3115324 | 11/1982 | Fed. Rep. of Germany. | |
| 2520636 | 1/1983 | France. | |
| 47-42254 | 10/1972 | Japan | 585/419 |
| 7609102 | 8/1976 | Netherlands. | |
| 8202272 | 1/1984 | Netherlands. | |
| 2033358 | 5/1980 | United Kingdom. | |
| 2114150 | 8/1983 | United Kingdom. | |

OTHER PUBLICATIONS

G. Wengui et al., "IR Study of Framework Vibrations and Surface Properties High Silica Zeolites", ZEOLITES, Elsevier Science, Amsterdam, 1985, pp. 279, 286.

Ione, Journal of Molecular Catalysis, 31, pp. 355-370 (1985).

Ione, "Structure and Reactivity of Modified Zeolites", ELSEVIR Science, (1984), pp. 151-155.

Huagong, vol. 15, No. 7 (1986) (with translation) 405-410.

Primary Examiner—Helen M. S. Sneed
Assistant Examiner—James Saba
Attorney, Agent, or Firm—Alexander J. McKillop; Charles J. Speciale; Marina V. Schneller

[57] ABSTRACT

A process for producing monosubstituted monoalkylaromatics from $C_8+$n-paraffins-containing feeds, by contacting the feeds with a non-acid catalyst comprising a microporous crystalline material containing tin, indium, thallium or lead, is disclosed.

33 Claims, 1 Drawing Sheet

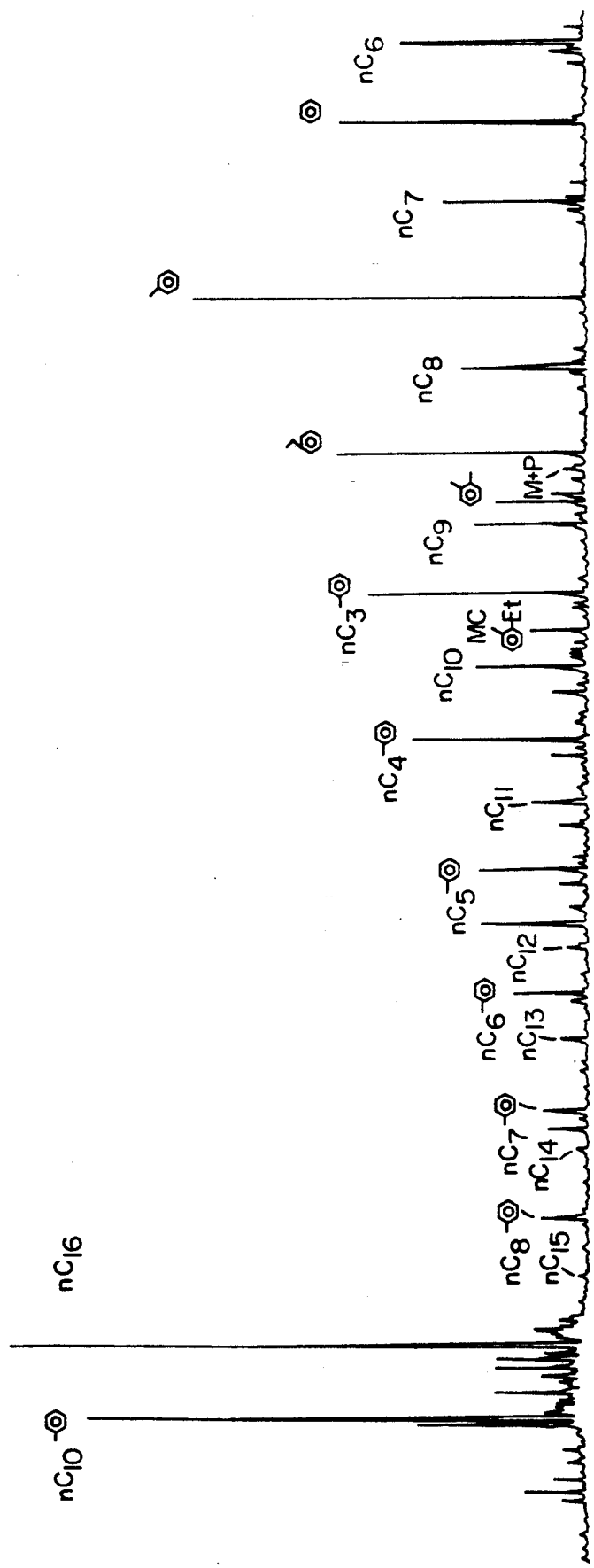

PRODUCTION OF MONO-SUBSTITUTED ALKYLAROMATICS FROM $C_8$+N-PARAFFINS

FIELD OF THE INVENTION

The invention relates to converting the $C_8$+n-paraffins in a feed to aromatic compounds, and particularly to monoalkyl aromatics such as ethylbenzene. The process comprises catalytic dehydrocyclization of the $C_8$+paraffins.

Enhanced yields of mono-substituted alkylaromatics from $C_8$+normal paraffins can be obtained over non-acidic dehydrogenation catalysts contained in intermediate pore size molecular sieves.

The non-acidic catalyst for the process substantially obviates the products of acid catalysis which can produce by-products of cracking and isomerization of hydrocarbons, both catalyzed by acidic catalysts. The non-acidic catalysts used in accordance with the invention include a Group VIII metal and a non-acidic microporous crystalline material containing tin, indium, thallium or lead modifier; the microporous crystalline material can be identified as an intermediate pore size molecular sieve.

Increased production selectivity of more linear mono-alkylaromatics from dehydrocyclization of n-paraffins may provide a more reliable source of chemical intermediates for synthesis of biodegradable sulfonate detergents.

BACKGROUND OF THE INVENTION

Non-acidic platinum catalysts are known to convert paraffins into aromatics under dehydrogenative conditions. In particular, the conversion of $C_8$+normal paraffins over a non-acidic Pt on alumina catalyst was reported (Davis and Venuto, JOURNAL OF CATALYSIS, Vol. 15, pages 363-372, 1969) to produce both mono- and di-substituted alkylaromatics, with the di-substituted isomers frequently dominating.

SUMMARY OF THE INVENTION

Non-acidic Group VIII metal containing catalysts comprising a microporous crystalline material support modified by indium, tin, thallium or lead enhance the selectivity of mono-substituted alkylaromatics from $C_8$+normal paraffins in a process which produces both mono-substituted and more bulky dialkyl aromatics by suppressing formation of the more bulky alkylaromatics, due to the shape selective properties of the support.

DESCRIPTION OF THE DRAWING

The Drawing is a GC trace of liquid product realized in Example 9.

DETAILED DESCRIPTION OF THE INVENTION $C_8$+normal-paraffins including $C_8$ paraffins are catalytically converted to monoalkyl aromatics. Preferably the $C_8$+paraffins are straight chain paraffins, i.e., $C_8$+normal-paraffins.

The catalytic conversion is effected by contacting the $C_8$+normal-paraffin-containing feed with a non-acidic catalyst comprising a Group VIII metal and a microporous crystalline material containing, as a modifier, tin, indium, thallium or lead, under conditions effective to convert the $C_8$+paraffin component(s) to monoalkylaromatic(s) product. The monoalkylaromatic product has preferably the same number of carbon atoms as the $C_8$+normal-paraffin.

The conditions effective to catalytically convert the $C_8$+normal-paraffins to the monoalkylaromatic analog include elevated temperature at pressures varying from subatmospheric to atmospheric and to greater than atmospheric. The conversion is conducted at elevated temperatures ranging from 300° to 700° C.; preferably, the temperatures range from 300° C. to 600° C.; and most preferably the temperatures ranges from 400° to 600° C. Reactor inlet $H_2$/feed ratios are 5 or less; even at reactor inlet $H_2$/feed ratios of zero (0), there will be a hydrogen partial pressure in the reactor because hydrogen is a byproduct of the catalytic conversion. Preferred pressures range from 0.1 atmospheres to atmospheric; however, pressures up to 500 psig can be employed. Liquid hourly space velocities can range from 0.1 to 50, preferably from 0.5 to 10.

The catalytic composition for the process of the invention comprises a non-acidic microporous crystalline material containing as a modifier tin, thallium, lead or indium. It has been discovered that these modifier containing microporous crystalline materials in non-acidic form combined with a Group VIII metal exhibit high selectivity for production of monoalkylaromatics, while exhibiting decreased selectivity for hydrogenolysis (especially methane formation) relative to their modifier-free counterparts.

The term "crystalline" used to refer to these materials relates to the ordered definite crystalline structure of the material which is unique and thus identifiable by a characteristic X-ray diffraction pattern.

The term "microporous" as it refers to such material relates to pores, or channels, with diameters of less than 20 Angstroms. Examples of these microporous crystalline materials include cyrstalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size an/or channel systems allow such a material to selectively absorb molecules of certain dimensions and shapes. In the art, microporous material having pores, or channels, of less than 20 Angstroms, can be divided into small, medium and large pore by the diameters of those pores.

The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimenson of 0.1 micron):

1. Small pore: $n$-$C_6$/$i$-$C_6$ sorption ratio greater than approximately 10.
2. Medium pore: $n$-$C_6$/$i$-$C_6$ is less than 10 and n-$C_6$/Mesitylene sorption ratio greater than approximately 5.
3. Large pore: $n$-$C_6$/Mesitylene sorption ratio less than approximately 5.

The modifier (tin, indium, thallium or lead) content of the crystalline microporous materials can range from 0.01 to 20 weight percent. Practically, the content will range from 0.1 to 10 weight percent.

The crystalline microporous modifier containing materials of the invention includes zeolites characterized by Si/Al ratios of at least 2. However, the silica:alumina ratio of the zeolite can be up to 1000, or greater. In a preferred embodiment the aluminum content of these materials is less than 0.1 weight percent and more preferably less than 0.02 weight percent.

The crystalline microporous modifier containing material used in the invention can contain other elements including boron, iron, chromium, and gallium. The content of these other elements in the crystalline modifier containing silicates can range from 0 to 10 weight percent.

The modifier containing crystalline materials of the invention, described herein, are crystalline in the sense that they are identifiable as isostructural with zeolites by X-ray powder diffraction pattern.

The crystalline microporous modifier containing material has an X-ray diffraction pattern which corresponds to a zeolite, SAPO, ALPO, etc.

In a preferred embodiment the pore size of the microporous crystalline modifier containing silicates ranges from about 5 to about 8 Angstroms. In a preferred embodiment an X-ray diffraction pattern of the microporous crystalline material containing modifier exhibits the structure of ZSM-5, ZSM-11, ZSM-22, or ZSM-23. The X-ray diffraction pattern of ZSM-5 has been described in U.S. Pat. No. 3,702,886 and U.S. Pat. No. Re. 29,948 each of which is incorporated by reference herein. ZSM-11, its preparation and X-ray diffraction pattern are described in U.S. Pat. No. 3,709,979, which is relied upon an incorporated by reference herein. ZSM-23, its preparation and X-ray diffraction pattern are described in U.S. Pat. No. 4,076,842, which is relied upon and incorporated by reference herein. ZSM-22, its preparation and X-ray diffraction pattern are described in Canadian Patent 1,210,747.

The amount of Group VIII metal in the catalyst can range from 0.01 to 30 weight percent and preferably 0.01 to 10 weight percent of the crystalline modifier containing material. In a preferred embodiment, platinum is the metal. However, the metal can be any Group VIII metal including those of the platinum group, chromium and vanadium.

The composition comprising metal combined with the crystalline containing silicates do not exhibit any appreciable acid activity. These catalysts would meet the criteria of non-acidic catalysts described by Davis and Venuto, JOURNAL OF CATALYSIS, Vol 15, page 363, 1969. Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When, as in embodiments herein, the crystalline modifier and metal containing material exhibits an X-ray diffraction pattern of a zeolite, at least some of the metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, JOURNAL OF CATALYSIS, Vol, 89, page 520, 1984. The test is based on the selective hydrogenation of olefins.

Compositions used in catalysis of the invention decrease the hydrogen content of the reactant to produce a product having at most the same number of carbon atoms as the number of carbon atoms in the reactant. Some of the aforementioned catalysts were screened for hexane and heptane aromatization at 538° C. in the presence of nitrogen diluent. The results are shown in Table A below in which the crystalline silicate employed exhibited the X-ray diffraction pattern of a ZSM-5.

TABLE A

Heptane Aromatization over Non-acidic Pt/ZSM-5

| Modifier | % Conv. | Toluene Sel. | Benzene Sel. | $CH_4$ Sel. |
|---|---|---|---|---|
| Sn | 99.3 | 95.0% | 1.5% | 0.4% |
| In | 98.2 | 92.7% | 1.8% | 0.5% |
| Pb | 98.7 | 95.4% | 1.1% | 0.4% |
| Tl | 99.6 | 85.7% | 6.7% | 1.7% |
| — | 96.3 | 40.9% | 19.4% | 9.3% |
| B | 94.7 | 30.2% | 32.8% | 20.7% |
| Cr | 95.5 | 44.4% | 20.4% | 3.4% |
| Ti | 96.1 | 31.8% | 32.6% | 19.7% |
| Sc | 96.3 | 38.9% | 40.6% | 16.0% |
| Au | 90.7 | 21.1% | 45.1% | 20.8% |
| Ni | 94.3 | 42.4% | 19.7% | 7.2% |
| Ge | 96.3 | 47.0% | 19.9% | 6.6% |
| Zr (470° C.) | 96.8 | 49.0% | 16.3% | 7.9% |

(a) 30 torr n-heptane in $N_2$ at 538° C. and 1 atm.; selectivities on $H_2$-free weight basis.

The non-acidic platinum catalyst prepared from thallium/ZSM-5, lead/ZSM-5, tin/ZSM-5 and indium/ZSM-5 provided much higher aromatics selectivity than all the other catalysts. Toluene selectivity from heptane was greater than 85% at 99% conversion ($H_2$ free carbon basis).

For comparison purposes, it should be noted that over dual functional platinum on acidic alumina reforming catalysts, the rate of heptane cracking to $C_6^-$ was twice the rate og dehydrocyclization. Cf J. H. Sinfelt, "Bimetallic Catalysts", J. Wiley, New York; p. 141 (1983).

The catalysts, including Pt/B-ZSM-5 and Pt/high silica:alumina ratio as well as those others enumerated in the Table did not show any appreciable acid activity, in that platinum chemistry dominated. Significant metal-catalyzed aromatization was observed; however hydrogenolysis to methane constituted a major competing side reaction. The highest toluene selectivity observed was 50-55%, and in most cases that selectivity was significantly lower. This is in sharp contrast to the aromatic product selectivity of the platinum/tin/ZSM-5, platinum/indium/ZSM-5, platinum/thallium/ZSM-5 and platinum/lead/ZSM-5. The cause for this difference in platinum behavior is not clear.

SYNTHESIS OF THE COMPOSITIONS

Methods for synthesizing tin and indium modifier containing zeolites are described in U.S. Pat. No. 4,868,145 and in allowed U.S. application Ser. No. 211,198 (filed Jun. 24, 1988), each of which is relied upon and incorporated by reference herein.

One way of incorporating the tin, indium, thallium or lead modifier into the composition of this invention is by incorporation during the synthesis of the non-acidic crystalline microporous material. Alternatively, the modifier can be incorporated with the crystalline composition post-synthesis of the microporous crystalline material. The metal can be incorporated during or after synthesis of the microporous crystalline material. The metal can be incorporated before, simultaneously with or after modifier incorporation.

Alternatively, reverse procedures can be applied in which the metal is first introduced with subsequent modifier incorporation. Stepwise preparation includes techniques of cocrystallization, impregnation, or exchange. Cocrystallization can be undertaken in a two phase system described in commonly assigned Ser. No. 878,555, filed Jun. 26, 1986. Other elements such as boron, iron, chromium, gallium, can also be included. Simultaneous incorporation includes the combination of modifier with the metal (e.g. platinum) during synthesis (i.e., crystallization) or simultaneously after synthesis of the crystalline material.

A modifier free material can be treated with compounds of the modifiers at elevated temperatures. Such treatments can be conducted so that the source of modifiers is either in the gaseous or the liquid phase including the aqueous phase such as tin II. Alternatively, a modifier free crystalline reactant can simply be impregnated with source of modifier and then calcined at temperatures above 400° C.

The modifier free reactant can have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by non-hydrogen (non-proton) and by non-hydrogen precursors, such as $NH_4+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described, for example, in U.S. Pat. No. 4,632,360.

In a preferred embodiment, the non-acidic crystalline microporous modifier containing silicates of the invention are treated with $Pt(NH_3)_4Cl_2$ in aqueous solution which has a pH of at least about 7 to incorporate the necessary platinum for catalyst composition formulation.

The non-acidic, crystalline, microporous, modifier and metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica.

EXAMPLES

Davis and Venuto reported that, over a non-acidic $Pt/Al_2O_3$ catalyst, n-octane yielded both ethylbenzene and xylenes, with xylenes in slight excess. The addition of tin to the catalyst (Davis et al, JOURNAL OF CATALYSIS, Vol. 42, pp. 247-256, 1976), further decreased the amount of ethylbenzene formed relative to xylenes.

In contrast, our non-acidic Pt/Sn-ZSM-5 catalyst produced ethylbenzene in greater than a two-fold excess over xylenes, as shown in Table 2 below.

A more dramatic effect was observed for n-nonane conversion. Whereas non-acidic $Pt/Al_2O_3$ reportedly yielded ethyltoluenes and n-propylbenzene in better than 2:1 ratio, Pt/Sn-ZSM-5 produced n-propylbenzene as the major product, exceeding the ethyltoluenes by more than a 3:1 margin.

TABLE 2

| Catalyst | Aromatization of n-Octane | | |
|---|---|---|---|
| | $Pt/AL_2O_3$ | $Pt/Sn-Al_2O_3$ | Pt/Sn-ZSM-5 |
| Temperature | 482° C. | 482° C. | 538° C. |
| Pressure | atm | atm | 50 psig |
| Carrier Gas | — | — | $N_2:H_2:HC$ ratio of 6:1:1 |
| $C_8$ Aromatic Selectivity: | | | |
| Ethylbenzene | 48% | 33% | 69% |
| Xylenes | 52% | 67% | 31% |

The following Examples describe the production of catalysts for the process of the invention.

EXAMPLE 1

Tin ZSM-5 silicate was synthesized in a static system at 300° F. 400 g 28.5% sodium silicate (Q-brand) was added to a solution of 60 g 50% tetramethylammonium chloride, 15 g $SnCl_4.5H_2O$, 30 g 98% $H_2SO_4$, and 60 g TPA+Br− in 2250 g water. The mixture was stirred and then place in a polypropylene bottle in an autoclave for five days. The product was 85% crystalline ZSM-5 and consisted of large 5-10 micron crystals. In this and following preparations the zeolitic silicates produced were characterized as having at least one crystal dimension which was at least 0.5 microns; it analyzed for 80.4% $SiO_2$, 0.30% $Al_2O_3$, 3.78% Sn, 2.00% Na, 7.70% C, and 1.05% N.

EXAMPLE 2

Another tin containing ZSM-5 sample was synthesized by dissolving 0.69 g Sn(II)SO$_4$ in 170 g de-ionized water and then adding 3.39 g NaOH. To this was added 6.38 g tetrapropylammonium bromide. The mixture was transferred to a 300 ml stainless steel autoclave and 16.0 g of a low aluminum content silica gel (SPEX Ind.) was added with stirring. The hydrogel formed by this reaction mixture is described by the following mole ratios:

| $SiO_2/Sn$ | $H_2O/Sn$ | $OH-/SiO_2$ | $Na+/SiO_2$ | $TPA+/SiO_2$ |
|---|---|---|---|---|
| 75 | 40 | 0.30 | 0.35 | 0.10 |

The hydrogel was reacted at 160° C. for five days with stirring (400 rpm) before quenching. The resulting crystalline product was processed in the usual manner by filtering, washing, and drying. X-ray diffraction anlysis of the product zeolite showed it to be 100% crystalline ZSM-5. SEM indicated an average crystal size greater than 2 microns.

EXAMPLE 3

A tin containing ZSM-5 sample was synthesized in a similar manner that the $SiO_2/Sn$ ratio was 150 and the $Na+/SiO_2$ was 0.31. The crystalline ZSM-5 product contained 1.36.% Sn, 0.0025% Al, 0.93% Na, and 89.31% Ash.

EXAMPLE 4

A tin containing ZSM-5 sample was synthesized in a similar manner except that the $SiO_2/Sn$ ratio was 50, the $Na+/SiO_2$ was 0.38, and the synthesis time was four days.

EXAMPLE 5

A tin containing ZSM-5 sample was synthesized at a $SiO_2/Sn$ ratio of 38, a $Na+/SiO_2$ ratio of 0.40, and a synthesis time of three days.

Tin incorporation was achieved during the zeolite synthesis, i.e., tin salts were added directly to the high silica ZSM-5 synthesis mixture. SEM data suggests that a significant portion of the tin is located outside of the large crystals formed. Nevertheless, some tin must be inside the ZSM-5 crystals, since it modifies the selectivity of the platinum, which itself is intracrystalline.

Platinum was incorporated by ion-exchange of the calcined zeolites, probably, via exchange for sodium ions associated with internal silyloxy groups. The presence of intracrystalline (intrazeolitic) platinum was confirmed by the extremely low benzene hydrogenation rates (TON=4 min$^{-1}$ at 100° C.) measured for these catalysts.

EXAMPLE 6

Platinum incorporation into the silicates of Examples 1-5 was undertaken. The as-synthesized tin silicates were calcined first in nitrogen and then in air at 520° C. The calcined materials were ion-exchanged with aqueous $Pt(NH_3)_4Cl_2$ at room temperature; typically, 15-20 mg per gram silicate was used in a non-acidic aqueous medium. The platinum tetramine-containing silicates were then calcined in oxygen to 350° C. at 0.5 C./min.

Elemental analysis of the tin silicate of Example 3 after platinum incorporation indicated Pt=0.80%, Sn=1.54%, Al=31 ppm.

Elemental analysis of the tin silicate of Example 1 after platinum incororation, Pt=0.65%, Sn=3.50%, Al=0.093%.

EXAMPLE 7

Thallium ZSM-5 silicate synthesis was undertaken as follow: A solution was prepared by dissolving 0.85 g $TlNO_3$ in 170.6 g di-ionized water and then by adding 2.05 g NaOH pellets. After all the base had dissolved, 6.38 g tetrapropylammonium bromide (TRAPr) was added. The resulting solution was transferred to a 300 ml stainless steel autoclave and 16.0 g of silica gel (SPEX Ind.) was stirred into the solution. The hydrogel produced can be described by the following mole ratios:

| $SiO_2/Tl_2O$ | $H_2O/SiO_2$ | $OH-/SiO_2$ | $Na+/SiO_2$ | $TPA+/SiO_2$ |
| --- | --- | --- | --- | --- |
| 150 | 40 | 0.20 | 0.21 | 0.10 |

The hydrogel was heated in the autoclave for four days at 160° C., with stirring at 400 rpm. The product was filtered, washed and dried. X-ray diffraction analysis indicated it to be 100% crystalline ZSM-5.

Elemental analysis indicated the presence of 8.26% C, 1.88% H, 0.74% N 0.34% Na, 4.33% Tl, 80.65% $SiO_2$, and 0.0095% Al in the ZSM-5 product.

EXAMPLE 8

Catalyst preparation was undertaken as follows: The as-synthesized thallium silicate was calcined, first in nitrogen and then air, at 520° C. The calcined zeolite contained 2.43% Tl, 38 ppm Al, and 43.15% Si.

Platinum was incorporated by ion exchange with $Pt(NH_3)_4Cl_2$ (15 mg/g zeolite) at room temperature. TGA ammonia titration in hydrogen indicated the presence of 0.67% Pt. The platinum-containing zeolite was then calcined in oxygen to 350° C. where it was maintained for one hour at 0.5° C./min.

EXAMPLE 9

In this example the catalyst comprised 1.5 g of Pt/Sn/ZSM-5 containing 0.8 weight percent platinum and 2.5 weight percent tin. The feed was n-hexadecane mixed with nitrogen and hydrogen in a $N_2:H_2:$n-hexadecane molar ratio of 6:1:1. The feed rate over the catalyst was 4 ml. per hour, under conditions including a temperature of 510° C., and a pressure of 50 psig, for several hours. Products were liquid at room temperature. 77 weight percent of liquid product was recovered. Gas chromatograph analysis indicated that the major products included n-alkyl aromatics, which included as major constituents n-alkyl aromatics, n-decylbenzene; and n-octylbenzene, n-heptybenzene, n-hexylbenzene and n-pentylbenzene, n-butylbenzene, n-propylbenzene, and ethylbenzene. See the drawing.

EXAMPLE 10

The preparation of the borosilicate ZSM-5 has been described. High silica:alumina ZSM-5 samples containing the elements: chromium, titanium, scandium, nickel, gold, germanium, and zirconium were synthesized in a manner analogous to that used to prepare Tl-ZSM-5, described above. The synthesis conditions are show in in Table 1 below:

TABLE B

| | | Synthesis of Metal-Containing ZSM-5 Mixture Composition (Mole Ratio) | | | | | |
| --- | --- | --- | --- | --- | --- | --- | --- |
| Example No. | Metal (M) Salt | $SiO_2/M$ | $H_2/SiO_2$ | $OH-/SiO_2$ | $Na+/SiO_2$ | $TPA+/SiO_2$ | Time Days |
| 5 | $Pb(NO_3)_2$ | 90 | 40 | 0.30 | 0.34 | 0.10 | 4 |
| 6 | $CrCl_3.6H_2O$ | 75 | 40 | 0.30 | 0.35 | 0.10 | 3 |
| 7 | $TiCl_4$ | 150 | 40 | 0.30 | 0.33 | 0.10 | 5 |
| 8 | $Sc(NO_3)_3.4H_2O$ | 75 | 40 | 0.20 | 0.21 | 0.10 | 4 |
| 9 | $Ni(NO3)3.6H_2O$ | 75 | 40 | 0.30 | 0.27 | 0.10 | 3 |
| 10 | $Au(OH)_3$ | 75 | 40 | 0.30 | 0.35 | 0.10 | 3 |
| 11 | $GeCl_4$ | 75 | 40 | 0.20 | 0.25 | 0.10 | 5 |
| 12 | $Zr(NO_3)_4$ | 75 | 48 | 0.26 | 0.31 | 0.10 | 3 |

(all syntheses used SPEX silica, temp = 160° C.), stirred

The synthesized zeolites all contained less than 0.06% Al and more than 0.4% Na. The final platinum-containing catalysts contained 0.57–0.80% Pt.

We claim:

1. A process for producing a monoalkylaromatic from a feed comprising a $C_8+$ n-paraffin comprising:
   contacting said feed comprising a $C_8+$ paraffin with a catalyst comprising 0.005 to 20 weight percent Group VIII metal and a non-acidic microporous crystalline material, under conversion conditions effective to produce said monoalkylaromatic wherein the microporous crystalline material exhibits the x-ray diffraction pattern of a medium pore size zeolite,
   and contains (a) 0.1 to 20 weight percent indium, tin, thallium, lead, or admixtures thereof and (b) less than 0.1 weight percent Al;
   converting said $C_8+$ paraffins to product comprising $C_8+$ monoalkylaromatic;
   and recovering the product.

2. The process of claim 1, wherein the Group VIII metal is platinum.

3. The process of claim 2, wherein the platinum satisfies the conditions to be designated intrazeolitic.

4. The process of claim 1, wherein the conversion conditions include a temperature ranging from 300° to 700° C. at pressure of 0.1 atmosphere to 500 psig.

5. The process of claim 1, wherein the zeolite is selected from the group consisting of ZSM-5, ZSM-11, ZSM-22 and ZSM-23.

6. The process of claim 1, wherein the crystalline material exhibits a Si:Al ratio of greater than 100.

7. The process of claim 1, wherein said feed is octane and said monoalkylaromatic is ethylbenzene.

8. The process of claim 1, wherein said feed is nonane and said monoalkylaromatic is n-propylbenzene.

9. The process of claim 1, wherein said feed is n-hexadecane and wherein each of said $C_8+$ monoalkylaromatics has a number of carbon atoms which is no greater than 16.

10. The process of claim 1, which further includes cofeeding hydrogen during said contacting.

11. In a process for converting $C_8+$ paraffins to aromatic compounds comprising a monoalkylaromatic compound and a dialkylaromatic compound, the improvement comprising
    contacting a feed comprising said $C_8+$ paraffins with a non-acidic catalyst comprising 0.005 to 20 weight percent of Group VIII metal and a microporous crystalline material comprising
    0.1 to 20 weight percent indium, tin, thallium, lead, or admixtures thereof;
    converting said $C_8+$ paraffins to product comprising $C_8+$ monoalkylaromatic;
    wherein the microporous crystalline material exhibits the x-ray diffraction pattern of a medium pore size zeolite,
    and recovering the product,
    in which product the ratio of monoalkylaromatic compound to dialkylaromatic compound is greater than 1.

12. The process of claim 11, wherein the microporous crystalline material exhibits the X-ray diffraction pattern of ZSM-5.

13. The process of claim 11, wherein the Group VIII metal is a platinum group metal.

14. The process of claim 11, wherein the Group VIII metal is platinum.

15. The process of claim 14, wherein the platinum satisfies the conditions to be designated intrazeolitic.

16. The process of claim 11, wherein the conversion conditions include a temperature ranging from 300° to 700° C. at pressure of 0.1 atmosphere to 500 psig.

17. The process of claim 11, wherein the crystalline material exhibits a Si:Al ratio of greater than 100.

18. The process of claim 11, wherein said feed is octane and said monoalkylaromatic is ethylbenzene.

19. The process of claim 11, wherein said feed is nonane and said monoalkylaromatic is n-propylbenzene.

20. The process of claim 11, wherein said feed is n-hexadecane and wherein each of said $C_8+$ monoalkylaromatics has a number of carbon atoms which is no greater than 16.

21. The process of claim 11, which further includes cofeeding hydrogen during said contacting.

22. The process of claim 1, wherein the microporous crystalline material contains less than 0.02 weight percent Al.

23. The process of claim 5, wherein the microporous crystalline material contains less than 0.02 weight percent Al.

24. The process of claim 11, wherein the microporous crystalline material contains less than 0.02 weight percent Al.

25. The process of claim 12, wherein the microporous crystalline material contains less than 0.02 weight percent Al.

26. The process of claim 15, wherein the microporous crystalline material contains less than 0.02 weight percent Al.

27. The process of claim 11, wherein the microporous crystalline material contains less than 0.1 weight percent Al.

28. The process of claim 12, wherein the microporous crystalline material contains less than 0.1 weight percent Al.

29. The process of claim 15, wherein the microporous crystalline material contains less than 0.1 weight percent Al.

30. The process of claim 11, wherein the zeolite is selected from the group consisting of ZSM-5, ZSM-11, ZSM-22 and ZSM-23.

31. The process of claim 27, wherein the zeolite is selected from the group consisting of ZSM-5, ZSM-11, ZSM-22 and ZSM-23.

32. The process of claim 28, wherein the zeolite is selected from the group consisting of ZSM-5, ZSM-11, ZSM-22 and ZSM-23.

33. The process of claim 29, wherein the zeolite is selected from the group consisting of ZSM-5, ZSM-11, ZSM-22 and ZSM-23.

* * * * *